(12) United States Patent
Weipert et al.

(10) Patent No.: US 6,540,987 B2
(45) Date of Patent: Apr. 1, 2003

(54) POLYESTERS BASED ON HYDROXY FATTY ACIDS AND LOWER HYDROXY ALKYL ACIDS AND USES THEREOF

(75) Inventors: Paul David Weipert, High Point, NC (US); Bharat B. Desai, Spartanburg, SC (US)

(73) Assignee: Ethox Chemicals LLC, Greenville, SC (US)

( * ) Notice: Subject to any disclaimer, the term of this patent is extended or adjusted under 35 U.S.C. 154(b) by 0 days.

(21) Appl. No.: 09/805,894

(22) Filed: Mar. 15, 2001

(65) Prior Publication Data

US 2002/0172646 A1 Nov. 21, 2002

(51) Int. Cl.$^7$ ................... A61K 7/06; A61K 31/765; A61K 9/14; C07C 229/00; C07C 69/66; C07C 69/73

(52) U.S. Cl. ................... 424/59; 424/497; 424/489; 424/70.11; 424/78.37; 424/78.08; 514/785; 560/171; 560/172; 560/176; 560/183; 525/400

(58) Field of Search ................... 424/497, 59, 489, 424/70.11, 78.37, 78.08; 514/785; 560/171, 172, 176, 183; 525/400

(56) References Cited

U.S. PATENT DOCUMENTS

| | | | | |
|---|---|---|---|---|
| 5,502,116 A | * | 3/1996 | Noda | 525/415 |
| 5,614,576 A | * | 3/1997 | Rutherford et al. | 524/270 |
| 5,851,937 A | * | 12/1998 | Wu et al. | 442/394 |

* cited by examiner

*Primary Examiner*—Sabiha Qazi
(74) *Attorney, Agent, or Firm*—Isaac A. Angres

(57) ABSTRACT

The present invention provides biodegradable polyesters based on lower hydroxy acids and hydroxy fatty acids. The resulting polyesters are useful as cosmetic vehicles for sunscreens, skin lotions and by themselves are also useful as milder skin exfoliants.

4 Claims, No Drawings

US 6,540,987 B2

POLYESTERS BASED ON HYDROXY FATTY ACIDS AND LOWER HYDROXY ALKYL ACIDS AND USES THEREOF

FIELD OF INVENTION

This invention relates to new biodegradable polymers and their use in the cosmetic field. The instant invention is also directed to biodegradable polyester polymers. This invention also relates to new biodegradable polyester polymers derived from hydroxy fatty acids and lower alkyl hydroxy acids or alkyl polyhydroxy diacids. The invention is further directed to cosmetic compositions containing biodegradable polyester. This invention further relates to biofriendly polyester polymers and copolymers derived from lactic acid, other hydroxy acids, ricinoleic acid and other hydroxy fatty acids. The present invention also relates to polyhydroxy polyalkanoates and their use as a vehicle for cosmetic products.

The present invention also relates to biodegradable polyester polymeric compositions especially poly[(lactic acid)-co-(ricinoleic acid)] and their use in cosmetic applications. The instant invention also relates to novel polyester polymers, polymer compositions and methods for using such polymers and compositions in personal care applications. In general terms, the polyester polymers and polymer compositions of the present invention are believed to be useful in the cosmetic treatment of keratin-containing substrates. Keratin substrates include, but are not limited to, animal and human hair, skin and nails.

More particularly, the instant invention relates to polyester polymer compositions and methods for treating keratin in which a cosmetically acceptable formulation is made with the instant polyesters as a cosmetic vehicle. Preferably, the cosmetically acceptable medium is a hair care product such as a shampoo, conditioner, styling product or rinse, or a skin care product such as a cleaner, lotion or cream.

The invention further relates to improved waterproof sunscreen compositions containing the polyesters of the instant invention.

The invention also relates to waterproof, high-SPF sunscreen compositions comprising an emollient/solvent system and sunscreen agent(s) in a polyester vehicle suitable for topical administration.

The invention is also concerned with waterproof sunscreen formulations and methods of protecting human skin from the effects of harmful ultraviolet radiation, e.g., erythema and burning, using effective amounts of the same.

BACKGROUND OF THE INVENTION

Even though cosmetic preparations have been a staple of commerce for centuries, there continues to be a continual expansion of cosmetic markets, and proliferation of new products. The field of skin care products has grown tremendously as new naturally occurring and synthetic polymeric materials have been identified. Processing equipment and techniques have also become more sophisticated, so that many of the current cosmetic products available over the counter, have a high level of uniformity and wholesomeness, but also impart substantive pharmacologic and nutritive properties not realized in older preparations.

The goal of modern cosmetics is to achieve multiple effects simultaneously, such as moisturizing, increased pliancy, drug or nutrient delivery, texturizing, environmental protection, and coloration. Some of these objectives inherently require substances which are water compatible such as humectants, and others require lipid compatible substances such as emollients. The largest class of cosmetic mixtures are emulsions of oil and water based fractions, and may be either oil in water (O/W) or water in oil (W/O), or both. For a review of the various physical forms and processes of making mixtures such as true emulsions, microemulsions, gels, and liposomes, see Fox, C., "Cosmetic Vehicles., Advances in Cosmetic Science and Technology, part 4," Cosmetics and Toiletries, 110: 59 (1995).

These emulsions have both occlusivity and humectancy. In occlusivity, a non-irritating moisture barrier is established on the surface of the skin, to prevent loss of moisture. Typical materials are petroleum jelly, mineral or vegetable oils, silicones, waxes, fatty acids, and esters. Typical humectants, which attract water and help bind water to the skin, include glycerin, sorbitol, sodium lactate, and sodium pyrrolidone carboxylate, are beneficial in hydrating the stratum corneum and improving its viscoelastic behavior (See Williams and Schmitt, eds., Chemistry and Technology of the Cosmetics and Toiletries Industry, 2nd ed., Blackie Academic and Professional, London: 1996).

Most emulsions require one or more stabilizers to maintain the microdispersion, and to prevent collapse and separation of the blend. A widely used stabilizer system utilizes stearic acid in the oil phase, and tri-, di-, or monoethanolamine in the aqueous phase. The resulting ethanolamine stearate is an excellent stabilizer. Combinations of intermediate chain length ($C_6$–$C_{12}$) aliphatic alcohols, esters, and carboxylic acids may act as stabilizers. Cetyl alcohol ($C_{16}$) is commonly used in conjunction with triethanolamine to impart both soft "feel" and stabilization of the emulsion. Cetyl palmitate, isolated from natural sources, is a preferred stabilizer and carrier for other ingredients.

Many cosmetic preparations require thickeners to provide the desired viscosity. These thickeners are often used when the lubricity of the oil fraction is heightened by a high unsaturated oil composition of the cosmetic. Typical thickeners include coconut diethanolamide, cellulose and certain ether derivatives such as hydroxyethylcellulose or hydroxypropylcellulose, carrageenan, which is a linear sulfated polysaccharide of D-galactose and D-anhydro-D-galactose. For a good discussion of the role of thickeners in cosmetic preparation, see Knowlton, et al., eds., Handbook of Cosmetic Science and Technology, 1st ed., Elsevier, Oxford: 1993).

Since the advent of polymer surfactant chemistry, a large and varied number of surface active compounds have been available for incorporation into cosmetics. Because surfactants tend to mobilize natural lipid, there is a pronounced tightening effect on the skin associated with their use, presumably by their residues binding to keratin. This effect is most severe using sodium lauryl sulfate, and is much diminished in the use of potassium myristate. The use of surfactants, of course, has an important cleaning function, so that they are common ingredients in cleansing creams. Since these creams are first spread onto the skin and then removed almost immediately by tissue wiping, surface contact is minimized.

There have been many studies of cosmetic additives which enhance the penetration of the beneficial ingredients into the lower strata of the epidermis. Similarly there have been many studies of the physiology, histology, and biochemistry of the epidermis and dermis and their relation to absorption. Among those compounds studied, the following have been identified as promoting adsorption and penetration (also termed "flux") of chemicals through the lipid-dominated interstices between cells of the lamellar layer: propylene glycol either alone or in combination with unsaturated fatty acids, and propylene glycol diesters of caprylic and capric acids. Solvents such as DMSO, ethanol, tetrahydrofuran, and isopropanol are known to deplete interstitial lipids leading to increased penetration of indicator drugs. These may be useful for "patch" type drug delivery devices, but have limited value in routine cosmetics because of their irritant properties. The goal of these ingredients is to promote adsorption and migration of beneficial substances through the lipid deposits without disrupting the essential structure of the skin.

A popular class of cosmetic additives (15 percent of total cosmetic sales) is the so-called sunscreens. UV light from the sum has a spectrum of wavelengths ranging from 400 nm down to less than 290 nm. Light having a wavelength of 400–320 is known as UV-A, that having a wavelength of 320–290 is called UV-B, and that having a wavelength of less than 290 nm is UV-C. UV-B has the greatest potential for causing skin damage and is associated with accelerating skin ageing, wrinkling, epidermal cracking and scaling, and more serious conditions such as basal cell carcinoma and melanoma. UV-A is associated with melanin production resulting in tanning. The desired function of a sunscreen is to absorb out the harmful UV-B light while allowing the UV-light to effect tanning. Ideally a sunscreen will shield the skin from a portion of the UV-A light as well as the UV-B because overexposure to UV-A can also cause skin damage.

Conventional sunscreen compounds that absorb UV-B light include benzophenone-3, benzophenone-4, and benzophenone-8, 4-methoxycinnamic acid salts, parabenzoic acid, substituted parabenzoic acid and salts thereof, glyceryl parabenzoic acid, menthyl anthranilate, $TiO_2$ and ZnO. UV-A is effectively absorbed by butyl methoxydibenzoyl methane. While most sunscreen compounds are spread onto skin in liquid form, dry compositions have been disclosed in U.S. Pat. No. 5,676,934. Other sunscreen formulations of interest are the stabilized preparations disclosed in U.S. Pat. Nos. 5,670,139, 5,573,755 (hydroxy salts of metallic ions), U.S. Pat. No. 5,543,136 (conventional titanium and zinc oxides in a smooth, even flowing emulsion stabilized with tridecyl polymers). Finally, certain compounds have been shown to enhance the activity and effectiveness of conventional classes of sunscreen compound disclosed in U.S. Pat. No. 5,607,664.

In the formulation of cosmetic preparations, most of the additive ingredients, e.g. humectants, sunscreens, surfactants, thickeners, etc. are present in low concentrations ranging from 0.1 to about 10 percent. Sunscreen concentrations are illustrative, and are also regulated by domestic and foreign governmental agencies, as set forth in the Cosmetic Handbook, supra: benzophenone-3 (2–6%), benzophenone-4 (5–10%), benzophenone-8 (3%), 4-methoxycinnimic acid salts (8–10%), para-aminobenzoic acid (1–5%), and butyl methoxydibenzoyl methane (5% maximum). The major difference in formulary is whether the emulsion is an O/W or a W/O. Obviously there will be a widely differing overall oil content in a W/O preparation. In the case of a high oil content all purpose cream, a typical will have sensory components (stearic acid, cetyl alcohol, microcrystalline wax, glyceryl monostearate and the like in a concentration of 0.5 to 3 percent, but the combination of mineral oil and petrolatum will approach 50 percent. In contrast, a hydroalcoholic astringent will contain nearly 50 percent ethyl alcohol, witch hazel extract, and glycerine.

In a low oil formulation, the oil content may be only a few percent, and the texture of the preparation will rely upon thickeners and emulsion stabilizers such as triethanolamine in combination with stearic acid.

There have been many variations of cosmetic preparations incorporating skin active agents in delivery systems of varying efficiency. U.S. Pat. No. 5,618,850 discloses a preparation incorporating alpha-hydroxy acid salts such as lactate and glycolate. The alpha-hydroxyacids have attracted much attention for their ability to control skin texture and wrinkling, and to confer beneficial effects in treating mild skin conditions. U.S. Pat. No. 4,393,043 is interesting in that it discloses the enrichment of cosmetic preparations with essential fatty acids including linoleic acid and conjugated linoleic acids, but only at the levels found in jojoba oil. In a similar disclosure in U.S. Pat. No. 4,661,343 an essentially anhydrous preparation utilizes karite oil to impart a mixture of fatty acids including linoleic acid in a concentration of 2 to 5 percent.

Many substances such as sunscreens and cosmetic creams are applied topically to the skin or mucous membranes of humans or animals (hereafter "skin") in order to alter the subject's appearance, to protect the subject from the environment, or to produce a biological change in the skin or other tissue for therapeutic, preventive or cosmetic purposes. These substances may generically be termed "topical products" and include such topically applied substances as cosmetics, over-the-counter and prescription topical drugs, and a variety of other products such as soaps and detergents.

Topical products occur in a variety of forms, including solids, liquids, suspensions, semisolids (such as creams, gels, pastes or "sticks"), powders or finely dispersed liquids such as sprays or mists. Examples of topical products commonly classified as "cosmetics" include skin care products such as creams, lotions, moisturizers and "treatment cosmetics" such as exfoliants and/or skin cell renewal agents; fragrances such as perfumes and colognes, and deodorants; shaving-related products such as creams, "bracers" and aftershaves; depilatories and other hair removal products; skin cleansers, toners and astringents; pre-moistened wipes and washcloths; tanning lotions; bath products such as oils; eye care products such as eye lotions and makeup removers; foot care products such as powders and sprays; skin colorant and make-up products such as foundations, blushes, rouges, eye shadows and liners, lip colors and mascaras; lip balms and sticks; hair care and treatment products such as shampoos, conditioners, colorants, dyes, bleaches, straighteners, and permanent wave products; baby products such as baby lotions, oils, shampoos, powders and wet wipes; feminine hygiene products such as deodorants and douches; skin or facial peels applied by dermatologists or cosmeticians; and others. Examples of topical products commonly classified as "topical drugs" are many and varied, and include over-the-counter and/or prescription products such as antiperspirants, insect repellents, sunscreens and sunburn treatments, anti-acne agents, antibiotics, topical respiratory agents, ocular drugs such as eyedrops and saline solutions, therapeutic retinoids, anti-dandruff agents, external analgesics such as capsaicin products, topical contraceptives, topical drug delivery systems, gastrointestinal agents such as suppositories, enemas and hemorrhoid treatments, reproductive system agents such as vaginal treatments, oral treatments such as lozenges, and many other products with therapeutic or other effects. Other topical products include hand, facial and body soaps and detergents and other forms of skin cleansers, as well as household detergents and many other household products such as solvents, propellants, polishes, lubricants, adhesives, waxes and others which are either applied topically or are topically exposed to the body during normal use.

In a large number of cases, topical products contain chemicals which may produce "irritation," including various inflammation symptoms or signs, when applied to the skin or mucosa. The present invention is directed in part to compositions and methods for inhibiting the irritation associated with such topical products.

The occurrence, frequency and nature of topical-product-induced irritation often varies from user to user. The severity of irritation to the susceptible user may range from subclinical to mild to severe. Typical symptoms of "irritation" include itching (pruritus), stinging, burning, tingling, "tightness," erythema (redness) or edema (swelling). The irritation response may be due to the direct effect on the skin of certain topical product chemicals or to a response by the immune system directed toward the chemicals alone or in combination with skin components (e.g. antigens).

The sensation of itch is one of the most common skin problems experienced by humans and animals. Itch can be defined as a sensation which provokes the desire to scratch the site from which the sensation originates. All skin contains sensory nerves which can transmit itch or other sensory impulses in response to chemical irritation, environmental exposure or disease processes. Although the precise population of itch producing nerves have not been identified, the thinnest, unmyelinated nerve population, termed type C nociceptive neurons are thought to be the most important in producing the sensation. Itch: Mechanisms and Management of Pruritus. Jeffrey D. Bernhard. McGraw-Hill, Inc. (San Francisco, 1994), pp. 1The sensory nerves of the skin can be considered to be a "final common pathway" for the many irritating conditions which may be ultimately sensed as itch including chemical exposure, environmental exposure (such as that which produces dry, itchy skin) and disease processes such as atopic dermatitis. Many chemical substances are able to produce itch or other sensory impulses when topically applied to the skin. No matter what the ultimate cause of itch, the sensation experienced is the same and provokes the desire to scratch.

Many ingredients used in topical products are known irritants or are potentially irritating, especially to people with "sensitive skin". These irritating ingredients include fragrances, preservatives, solvents, propellants and many other ingredients that might otherwise be considered inert components of the products. Additionally, many topical product active ingredients, including chemicals that may also be classified as drugs, produce irritation when applied to the skin. These include, but are not limited to, such ingredients as exfoliants and skin cell renewal agents, anti-acne drugs, antiperspirant compounds, antihistamines, anti-inflammatory agents, skin protective agents, insect repellent chemicals, sunscreens and many others. Where more than one chemical irritant is present, their irritating effects may be additive. Furthermore, chemical ingredients may react with one another, or in the environment of the skin, to form new chemicals which are irritating. The vehicles in which the active drug ingredients are formulated may also produce irritation in sensitive people, especially in the case of drugs such as topical corticosteroids.

In addition to chemicals which directly trigger skin irritation, some chemicals indirectly cause the skin to become more sensitive to other chemicals or environmental conditions which would not normally cause irritation. Many chemicals which act as skin "exfoliants" such as retinoids (e.g. tretinoin, retinol and retinal), carboxylic acids including α-hydroxy acids (e.g. lactic acid, glycolic acid), β-hydroxy acids (e.g. salicylic acid), α-keto acids, acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, benzoyl peroxide and phenol, among others, may cause the skin to become more sensitive to irritation triggered by other topically-applied chemicals such as moisturizers, sunscreens, fragrances, preservatives, surfactants (e.g. soaps, shaving cream) and other topical products. Exfoliants and other ingredients may also increase the skin's sensitivity to environmental conditions such as sunlight, wind, cold temperature and dry air, or to chemical agents such as antigens, or may exacerbate the irritation attributable to a pre-existing skin disease.

Conversely, environmental influences may themselves increase the skin's sensitivity to chemicals in topical products by reducing the epidermal skin's "barrier function." The barrier function acts to minimize absorption or passage of potentially irritating chemicals through the outer "dead" cell layer of epidermal skin into the living skin tissue.

Extremes of humidity, for example, can greatly increase irritation from topically-applied products. A very common condition due to low humidity is termed "winter itch" in which the very low humidity characteristics of many cold climates (particularly when accompanied by indoor heating) or long exposure to refrigerated air from air conditioners in the summer produces itchy skin—especially in older people—which can exacerbate the irritating effects of topical products. Additionally, soaps, detergents, cleansing products, shaving creams, alcohol and other products which remove some of the skin's protective lipids and/or secretions may increase the skin's permeability and sensitivity to topically-applied chemicals which would otherwise not produce irritation. Normal processes such as sweating may also increase the ability of irritant materials, such as antiperspirants, deodorants or sunscreens, to penetrate the skin through pores or glands, thus exacerbating the potential for irritation. Exposure of the skin to high humidity environments or liquids may also increase the ability of potential irritants to penetrate the skin. Similarly, the skin may become sensitized or inflamed due to infection, shaving abrasion, repeated or excessive washing or bathing, sun exposure, or other mechanical abrasion or injury, resulting in sensory irritation responses upon subsequent application of underarm deodorants, after-shaves or other topical products.

In addition to chemical and environmental causes of skin irritation, many people have an inherent sensitivity or genetic predisposition to skin irritants. People with respiratory allergies, for example, tend to have excessively dry skin which facilitates increased absorption of potentially irritating chemicals. The excessively dry skin which accompanies atopic dermatitis, for example, predisposes patients with this condition to irritation from many topically-applied products. Other skin diseases and conditions such as allergic or non-allergic contact dermatitis, asthma (including exercise-induced asthma as may be precipitated by inhalation of cold or dry air), rhinitis, conjunctivitis, inflammatory bowel disease, psoriasis, eczema, post-herpetic neuralgia, infectious diseases manifested by, for example, sore throat or skin lesions such as candidiasis, insect bites and the like produce intrinsic irritation which may be exacerbated by application of topical products or by exposure to chemical or environmental influences such as antigens, cold air, low humidity and the like. Many other individuals exhibit sensitive skin as a condition that is not related to an identifiable skin disease.

Whatever the exact cause of irritation, many attempts have been made to reduce the irritation potential of topical products by identifying chemicals which tend to cause irritation and reducing their concentration or eliminating them from the products. Many of these products are advertised to consumers as "hypoallergenic" or the like to designate a product's reduced tendency to cause irritation in consumers with sensitive skin. Many skin (including mucosal) irritation responses, however, are not allergic in origin. In any event, it is often not feasible or practical to identify or eliminate all of the irritating chemical(s), particularly when the irritating chemical(s) are the active ingredient of the product or are required for formulation, preservative or other functional reasons.

As one example, there is a substantial practical and commercial need in the field of exfoliants and related skin care products for a composition or method that will reduce or prevent the irritation caused by such products. Common exfoliants include α and β-hydroxy carboxylic acids such as lactic acid, glycolic acid, salicylic acid and the like, α-keto acids such as pyruvic acid, as well as assorted compounds such as acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, peroxides, phenols, and skin cell renewal agents such as retinoids. Such products are used as exfoliants and/or cell renewal agents to reduce the occurrence or severity of skin wrinkles, particularly facial wrinkles, or as anti-acne, anti-"dry skin" or skin whitening agents. See U.S. Pat. Nos. 4,105,782, 4,105,783, 4,246,261, and 5,091,171 (Yu et al.) and U.S. Pat. No. 5,262,153 (Mishima et al.); W. P. Smith, "Hydroxy Acids and Skin Aging," Soap/Cosmetics/Chemical Specialties for September 1993, p. 54(1993). Hydroxy acids, in concentrations high enough to exfoliate, are well known often to cause skin irritation and rashes. The danger of irritation is even higher for persons that have sensitive skin.

Although there have been significant advances in the art of waterproofing sunscreen lotions and also improving their skin moisture retention properties, there still remains considerable need for improvements. For instance, it is desirable to formulate a composition not including any hydrophobic resins. These resins leave undesirable residues upon the skin and also give rise to stability problems. Stability against phase separation during freeze-thaw cycles is an important goal for formulators. Finally, there is also the need to reduce irritancy of the sunscreen products.

OBJECTS OF THE INVENTION

It is a first object of the present invention to provide novel bio-friendly polyesters.

It is another object of the instant invention to provide novel bio-degradable polyesters.

A further object of the invention is to provide novel bio-friendly polyesters useful as cosmetic vehicles.

A still further object of the invention is to provide novel bio-degradable polyesters useful as cosmetic vehicles.

An additional object of the invention is to provide novel bio-friendly polyesters derived from hydroxy acids and hydroxy-fatty acids.

A still further object of the invention is to provide improved bio-friendly cosmetic vehicles derived from hydroxy acids and hydroxy-fatty acids.

An additional object of the present invention is a biodegradable cosmetic vehicle from hydroxy acids and hydroxy-fatty acids.

Another main object of the present invention is to provide cosmetic compositions having excellent water resistance.

Another object of the present invention is to provide topical bio-friendly cosmetic compositions having a vehicle derived from hydroxy acids and hydroxy-fatty acids.

A still further object of the present invention is to provide a sunscreen composition having a relatively low human irritancy.

An additional object of the invention is a method for treating skin wrinkles and aging of the skin by topically applying to said skin an effective amount of an alpha or beta hydroxy acid polyester of the present invention.

These and other objects of the present invention will more readily become apparent from the description and examples which follow.

SUMMARY OF THE INVENTION

The present invention is directed to biodegradable polyester polymers of the formula I:

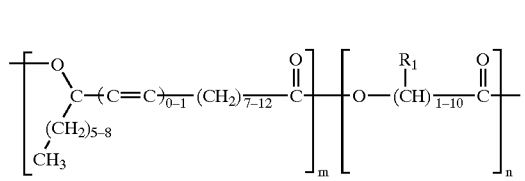

wherein $R_1$ is selected from the group consisting of hydrogen and $C_{1-5}$ alkyl, m and n are independently integers from 1 to 100, and m+n is an integer from 2 to 100.

The present invention also provides a biodegradable polyester of the formula II:

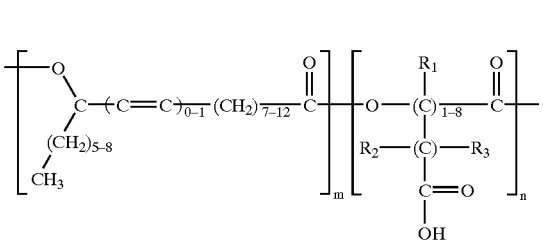

wherein $R_1$ is selected from the group consisting of hydrogen and $C_{1-5}$ alkyl; $R_2$ is selected from the group consisting of hydrogen and hydroxy; and $R_3$ is selected from the group consisting of hydrogen and $C_{1-5}$ alkyl, m and n are independently integers from 1 to 100, and m+n is an integer from 2 to 100.

The invention further provides a biodegradable polyester of the formula III:

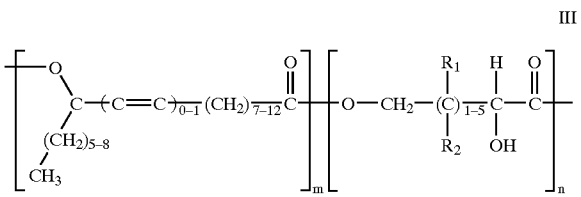

wherein $R_1$ and $R_2$ are selected from the group consisting of hydrogen and $C_{1-5}$ alkyl, m and n are independently integers from 1 to 100, and m+n is an integer from 2 to 100.

The invention additionally provides polyesters of the formula IV:

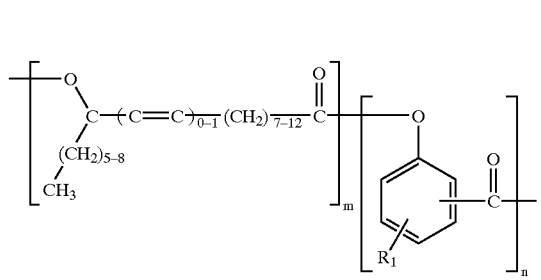

wherein $R_1$ is selected from the group consisting of amino, carboxyl and hydrogen, m and n are independently integers from 1 to 100, and m+n is an integer from 2 to 100.

The invention also relates to a water-proof sunscreen composition comprising:

(a) from about 2% to about 98% by weight of a polyester according to formulas I, II, III and IV as defined above; and (b) from about 1.0% to about 30.0% by weight of an active ultraviolet radiation absorber.

The instant invention further relates to a method for treating skin wrinkles and aging of the skin which method comprises topically applying to said skin an effective amount of an alpha or beta hydroxy acid polyester selected from the group consisting of Poly[(lactic acid)-co-(ricinoleic)], polyglycolate ricinoleate, polysalicylate ricinoleate and their hydrogenated derivatives in a cosmetically acceptable carrier.

DESCRIPTION OF THE PREFERRED EMBODIMENTS

In the first preferred embodiment, the present invention is directed to biodegradable and bio-friendly polyesters derived from the reaction of monohydroxy acids and hydroxy-fatty acids having the formula I

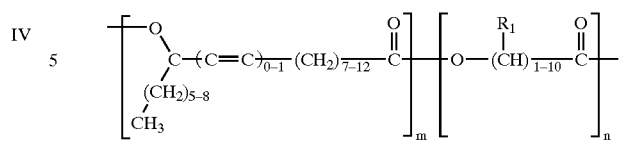

wherein $R_1$ is selected from the group consisting of hydrogen and $C_{1-5}$ alkyl, m and n are independently integers from 1 to 100, and m+n is an integer from 2 to 100. The m to n ratio is typically from about 80:20 to about 20:80, more preferably from about 60:40 to about 40:60 and most preferably 50:50. The polyesters of the present invention are made by reacting in a conventional reactor suitable for esterification or transesterification reactions and at an elevated temperature range of from about 150° C. to about 220° C. under agitation conditions, a monohydroxy acid such as lactic acid with a hydroxy fatty acid such as ricinoleic acid or its methyl ester or the hydrogenated derivatives of said fatty acids. The reaction is conducted for a period of time sufficient to produce the equivalent amount of water or alcohol based on the equivalent ratios of reactants. Of course, as is well known in the field of organic chemistry, the water or alcohol that is produced during esterification or transeterification is azeotropically removed during the reaction to drive the reaction equilibrium to the right. Typical hydroxy acids that can be used in the practice of the present invention include glycolic acid, lactic acid, lactide (lactic acid dimer) 4-hydroxybutyric acid, 5-hydroxypentanoic acid, 6-hydroxy-hexanoic acid, 11-hydroxyundecanoic acid, malic acid, citric acid, tartaric acid, salicylic acid, aminosalicylic acid and fatty acids such as ricinoleic acid and hydrogenated ricinoleic acid ie., 1-hydroxy stearic acid and their respective lower $C_1$–$C_2$ esters and glycerides thereof. The reaction of the above hydroxy-acids with for example ricinoleic acid can be exemplified as shown below for the initial formation of e.g., the trimer ester and then the resulting polyester with further polymerization:

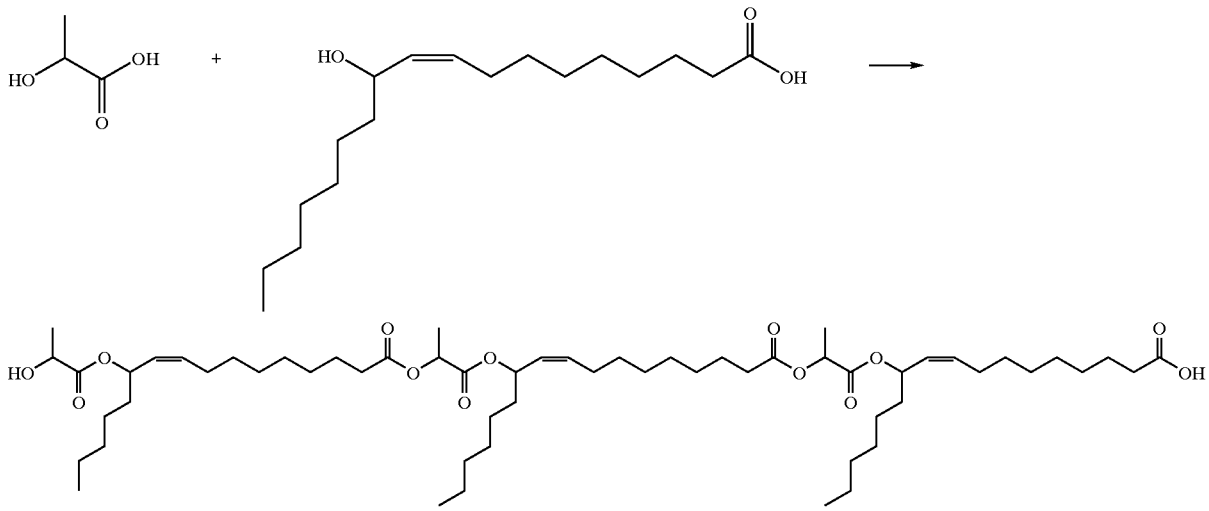

Other trimeric and also dimeric species contemplated by the present invention are exemplified by the chemical structures shown below, however it should be noted that in the polymeric structures, the repeating mer structures repeat each other many times. The trimeric species are for purposes of illustration:

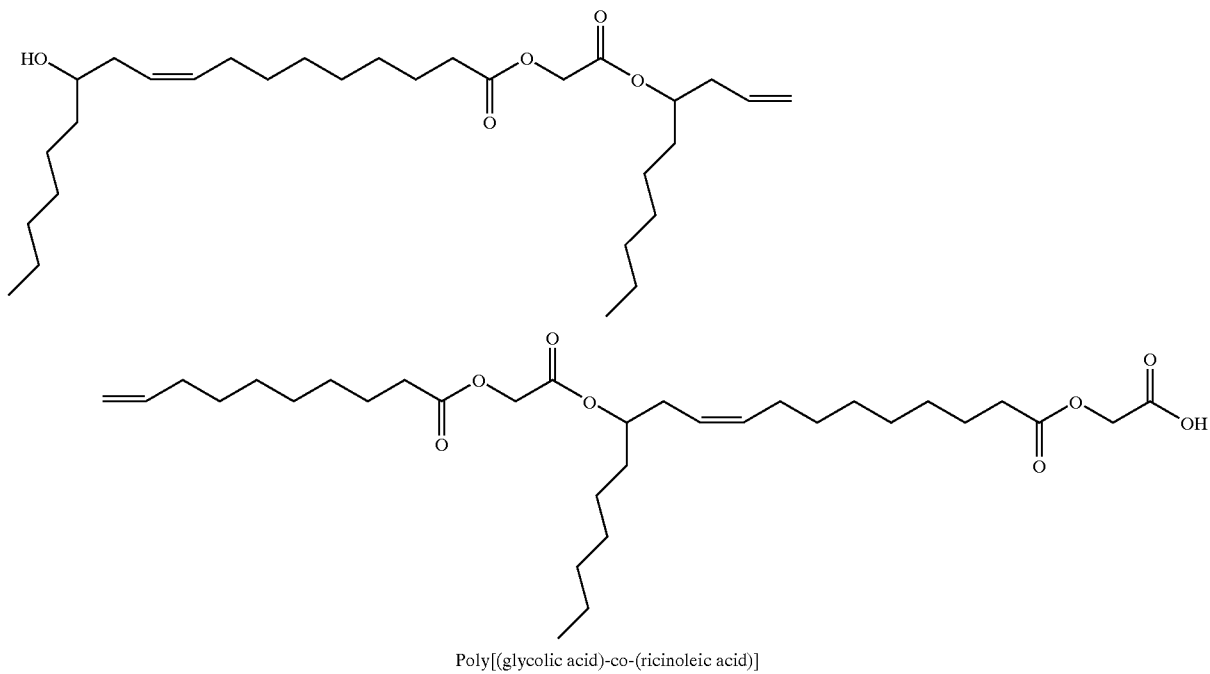

Poly[(glycolic acid)-co-(ricinoleic acid)]

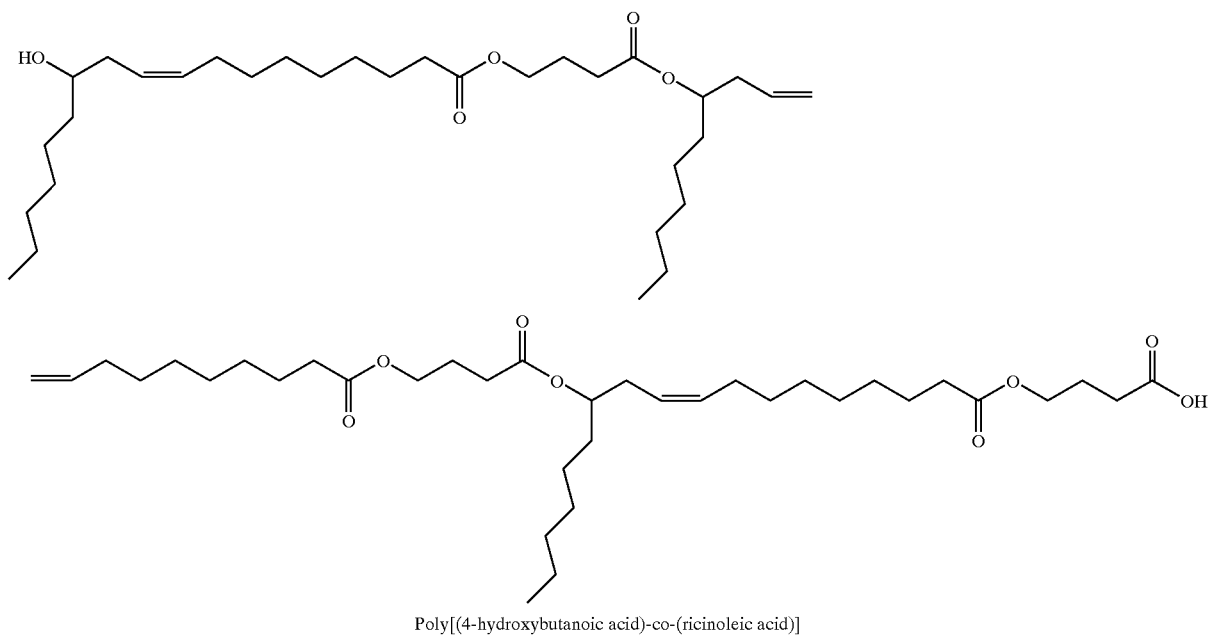

Poly[(4-hydroxybutanoic acid)-co-(ricinoleic acid)]

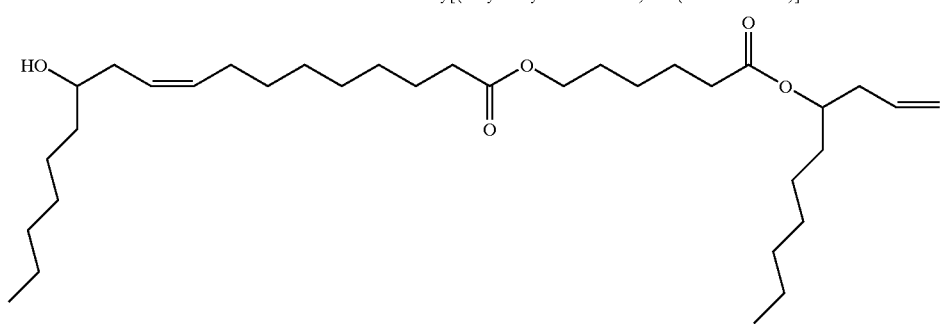

-continued

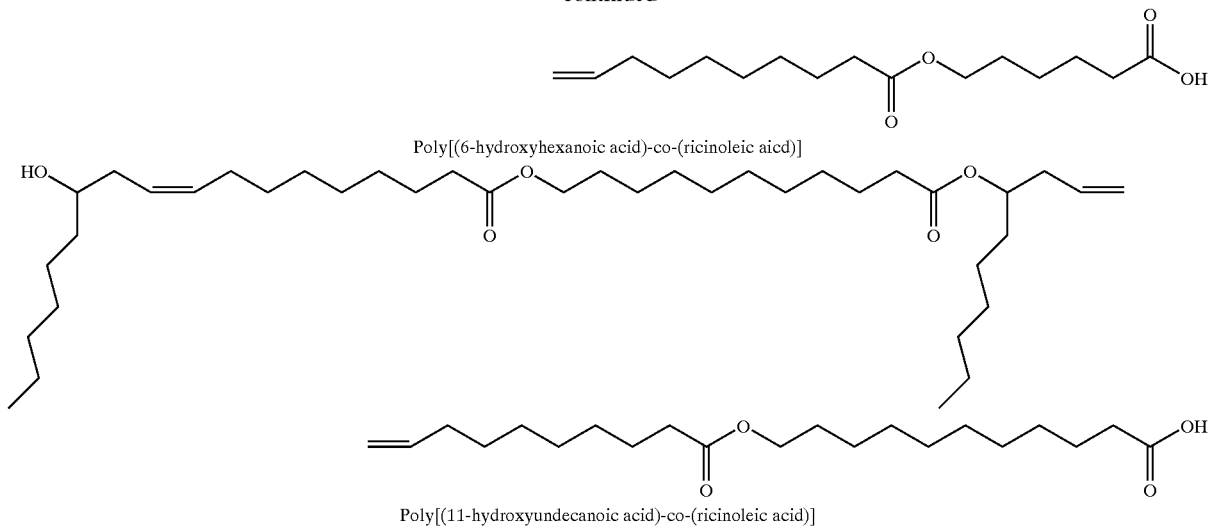

Poly[(6-hydroxyhexanoic acid)-co-(ricinoleic aicd)]

Poly[(11-hydroxyundecanoic acid)-co-(ricinoleic acid)]

The resulting polyesters of the invention are random co-polymers of the hydroxy acid and the hydroxy fatty acid and they have an average molecular weight of approximately 2500 as determined by the acid value of the end group, where acid value is defined as milligrams of potassium hydroxide per gram of sample. Of course polymers of higher molecular weights can be made by running the reaction for longer time, or at a higher temperature or by selecting the proper catalyst.

The design of the new polymers of the invention utilizes the double bond of the ricinoleic acid to keep the polymer in the liquid state while the hydroxy acid portion of the polymer gives flexibility as it regards water solubility, biodegradability and compatibility with the skin.

Polymers with different degrees of polymerization have been made which correspond to the formula

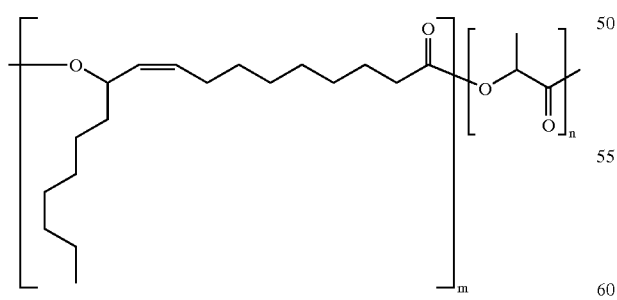

and having the following properties:

| m + n value | AV |
|---|---|
| 4 | 37.9 |
| 5 | 30.3 |
| 6 | 25.3 |
| 7 | 21.7 |

In a second preferred embodiment, the invention is directed to biodegradable and bio-friendly polyesters derived from the reaction of polyhydroxy acids or hydroxy polyacids and hydroxy-fatty acids having the formula II

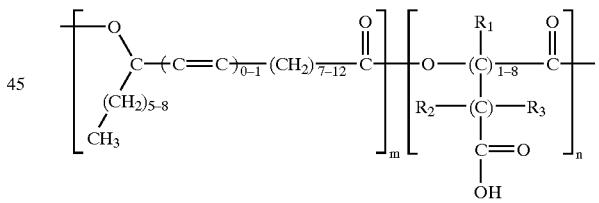

wherein $R_1$ is selected from the group consisting of hydrogen and $C_{1-5}$ alkyl; $R_2$ is selected from the group consisting of hydrogen and hydroxy; and $R_3$ is selected from the group consisting of hydrogen and $C_{1-5}$ alkyl, m and n are independently integers from 1 to 100, and m+n is an integer from 2 to 100. The m to n ratio is typically from about 80:20 to about 20:80, more preferably from about 60:40 to about 40:60 and most preferably 50:50.

Typical polymers represented by polyesters of formula II are structurally exemplified below. For the malic acid polyester, the structural formula is as follows:

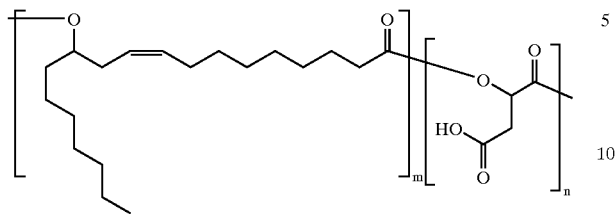

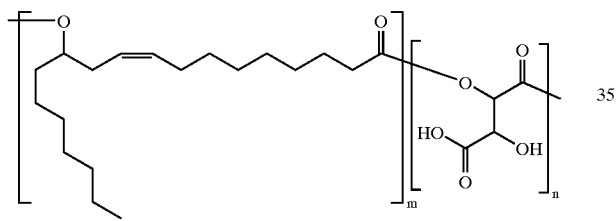

For the tartaric acid polyester, the structural formula is as follows:

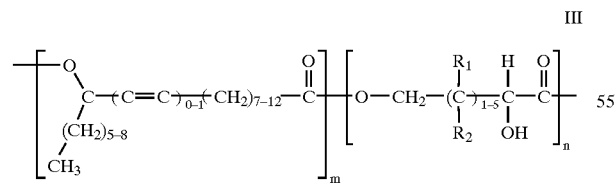

The above polyesters are prepared in a similar manner as described above for the reaction of the monohydroxyacids and the hydroxyfatty acids i.e., by heating the hydroxyfatty acid with the polyhydroxy acid or the hydroxypolyacid with a suitable catalyst and for a period of time sufficient to remove azeotropically the equivalent amount of water depending on the ratio of reactants.

In a third embodiment, the invention is directed to a biodegradable polyester of the formula III:

III

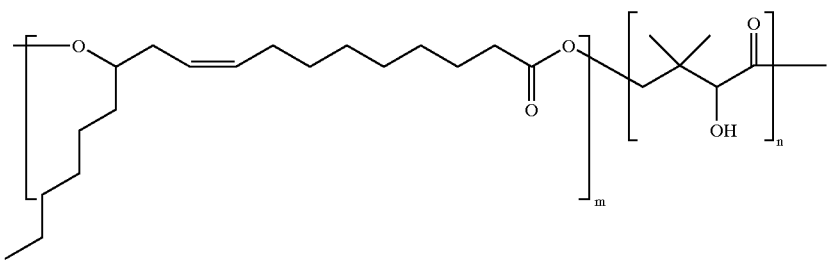

wherein $R_1$ and $R_2$ are selected from the group consisting of hydrogen and $C_{1-5}$ alkyl, m and n are independently intergers from 1 to 100, m+n is an integer from 2 to 100. The m to n ratio is typically from about 80:20 to about 20:80, more perferably from about 60:40 to about 40:60 and most perferably 50:50.

A specific example corresponding to the generic polymer structure is the polymer of ricinoleic acid and pantolactone and having the following chemical structure:

In a fourth embodiment, the invention is directed to polyesters of the formula IV:

IV

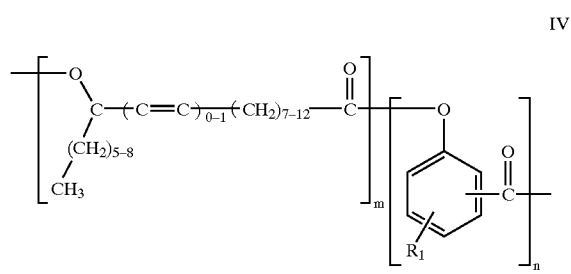

wherein $R_1$ is selected from the group consisting of amino, carboxyl and hydrogen, m and n are independently integers from 1 to 100, and m+n is an integer from 2 to 100. The m to n ratio is typically from about 80:20 to about 20:80, more preferably from about 60:40 to about 40:60 and most preferably 50:50.

The synthesis of the above polymers is the same as described above for polymers having structures I, II or III.

Specific examples of polymers corresponding to structure IV include the polymers of ricinoleic acid and salicylic acid having the following chemical structure

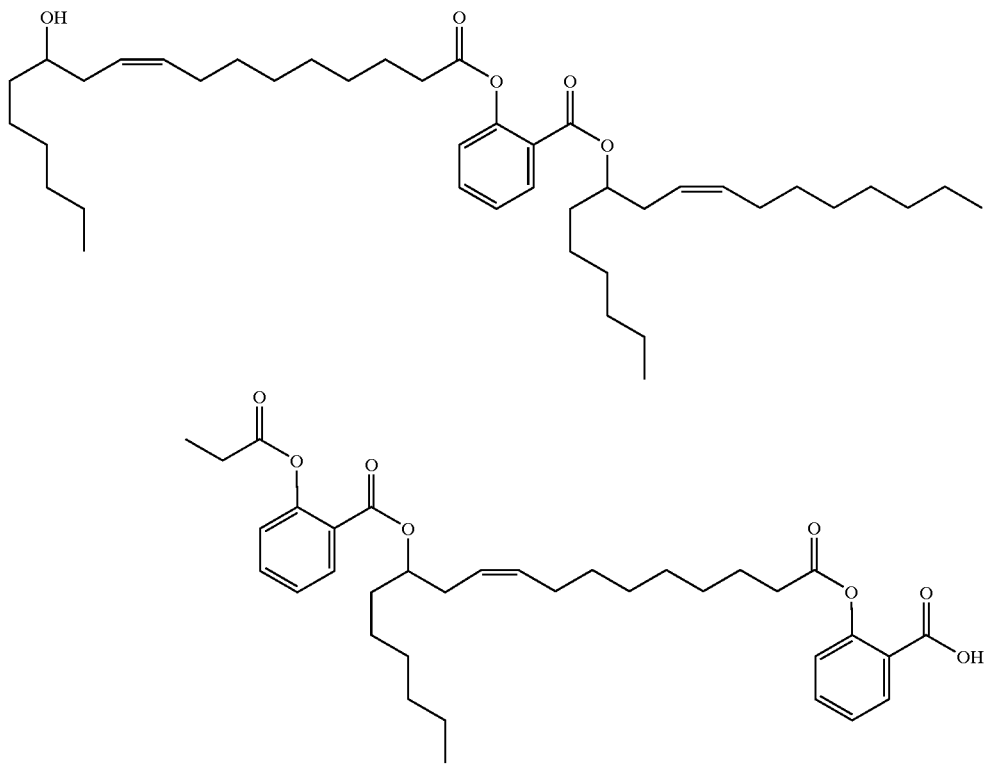

Of course the polymers of the fully saturated hydroxy fatty acids are also manufactured in a similar manner as the ones with one double bond to produce the polymers without the double bond and accordingly increase the hydrophobicity of the polyesters.

Since the polyesters of the present invention are mild to the skin, they are particularly useful for cosmetic applications although they also could be used as a prodrug precursor of the lower hydroxy-acids i.e., the use of α- and β-hydroxy acids in skin exfoliation. Preferred polyester of the present invention for cosmetic applications have an average molecular weight from about 600 to about 5000. The present composition may contain up to 98% of the polyester of the present invention. The preferred amount of polyester is from about 30% to about 70% and most preferably from about 40% to about 60%. Amounts of less than 30% are also acceptable if used in combination with water-insoluble liquid emollients, volatile liquid carriers such as Isopropanol or volatile silicone fluids. Compositions containing levels of 5% by weight of polyester of the present invention having an average molecular weight from 600 to about 5000 when used in combination with water or liquified propellants, such as Isobutane and Propane, provide adequate application to the skin with acceptable drying time and overall aesthetics.

It will be understood that if one replaces any portion of the polyester of the present invention, with one ingredient or a mixture of any ingredients mentioned in this invention that do not have degrees of hydrophobicity and adhesion to the skin similar to that of the polyester of the present invention, compositions prepared with these ingredients or a mixture of these ingredients, will have their drying rates, water resistancy, sunscreen efficacy and overall cosmetic aesthetics reduced. However, so long as the final compositions have at least 5% polyester of the present invention by weight, these compositions will still be more water resistant and effective than compositions without the use of the polyester of the present invention. It will be further understood that the polyester of the present invention provide excellent compatibility with an array of cosmetically acceptable ingredients, and any ingredient combination may be made without departing from the spirit and scope of this invention.

The present composition may additionally contain, as an optional ingredient, from about 0% to about 20% by weight of suspended particulate solid matter which is insoluble in the ingredients used in the composition. From these solids a group of solids have been selected which are inert in the composition, having a low degree of irritation and toxicity, that are generally considered safe for topical use, that provide for a cosmetic benefit and reflect and/or absorb ultraviolet radiation. Solids that are used for cosmetic purposes are solid materials that produce a "glitter", "sparkle" or "pearlesant" effect when exposed to natural or artificial light. Preferred solids for cosmetic purposes include such solids as bismuth oxychlorid, mica and colorized acrylic polyester. The preferred solid in the present composition, for cosmetic use, is the colorized acrylic polyester. The preferred amount of solid used for cosmetic purposes in the present invention is from 0.5% to about 10% by weight.

The preferred solid used in the present invention for the purpose of reflecting or absorbing ultraviolet radiation are solids such as zinc oxide, and titanium dioxide. These solids are generally used in a powder form in which the average particle size is less than 100 microns. The preferred amount of suspended particulate solid matter used in the present invention for the purpose of reflecting ultraviolet radiation is from about 5% to about 15% by weight.

The present composition may also contain, as an optional ingredient, from about 0% to about 15% by weight of a thickening agent. Thickening agents, which can be used in the present invention are ingredients that have a propensity for hydrophobic compounds, that allow the formation of a laminated network of thickening agent molecules producing an increase in the viscosity of the composition, which are non-irritating, non-toxic and are compatible with the ingredients used in the composition which when applied to the skin allow the formation of a continuous polymeric film in which the active sunscreen agent is homogeneously dispersed. Examples of such thickening agents are selected from a group consisting of synthetic polymers such as polyethylene polymers sold under the Tradename of AC Polyethylene by (Allied Chemical, Morristown, N.J.); organic salts such as zinc stearate; fatty acids such as stearic, fatty alcohols such as myristyl, esters such as glycerol stearate; Natural waxes such as paraffin, carnauba, spermaceti, and microcrystalline; inorganic salts such as fumed silica, amorphous silica, sodium magnesium silicate and colloidal magnesium aluminum silicate. The preferred thickener is zinc stearate. Cellulosic ethers such as hydroxypropyl cellulose are also preferred. The preferred amount of the thickening agent is from 0.5% to about 8% by weight.

The cosmetic compositions of the present invention also incorporate surface active agents. Surface active agents used in the present composition are defined as surface active agents that allow for the formation of emulsions preferably water-in-oil emulsion, which are viscous lotions or creams consisting of the polyester of the present invention, active sunscreen agent, water and any optional ingredient used in the compositions of the present invention.

The function of the surface active agents used in the present invention which are used for the purpose of forming an emulsion is to physically unite the polyester of the present invention, active sunscreen agent and water, which are not compatible under normal conditions, by decreasing the interfacial tension, and allowing the formation of hydrogen bonding in which sub-micron particles of polyester of the present invention/active sunscreen agent are formed and remain suspended for long periods of time throughout the water media.

Surface active agents which can be used in the present invention for the purpose of forming viscous lotion or cream emulsions are those which are non-irritating, non-toxic and are compatible with the ingredients used in the composition which when applied to the skin allow the formation of a continuous polymeric film in which the active sunscreen agent is homogeneously dispersed which are selected from a group consisting of anionic surfactants such as alkanolamides, and alkyl ether sulfates; nonionic surfactants such as ethers derived from the condensation of fatty acids and ethylene oxide; and of soaps of fatty acids such as ammonium myristate, triethanolamine stearate and potassium oleate.

The preferred surface active agents are soaps of fatty acids and those which are nonionic in nature which have a tendency to form water-in-oil emulsions. To those skilled in the arts, there are numerous known varieties of nonionic surface active agents which will form such emulsions. Since the overall hydrophile-lipophile balance of an emulsion is the prime factor in emulsion formation, which includes all of the ingredients in the composition and most specifically those ingredients which are to emulsified, applicant wishes not to be limited to any specified surface active agents. It will be further understood that the surface active agents provide excellent compatibility with an array of cosmetically acceptable ingredients, and any combination may be made without departing from the spirit and scope of this invention. The present invention may optionally contain from about 0% to about 15% by weight of the surface active agents described heretofore. The preferred amount of surface active agent used in the present composition for the purpose of forming an emulsion is from about 2% to about 6% by weight.

The present composition may also contain, as an optional ingredient, from about 0% to about 85% by weight of a liquified propellant. Any liquified propellant, capable of producing a sufficient vapor pressure for expelling the composition from a conventional aerosol container which, is non-irritating, non-toxic and is compatible with the ingredients used in the composition and when applied to the skin allows the formation of a continuous polymer film in which the active sunscreen agent is homogeneously dispersed, can be used. Propellants that meet these criteria are: butane; isobutane; propane; dimethyl ether; dichlorodifluoromethane; tetrafluoromethane; dichlorotetrafluoroethane; chlorodifluoromethane; chlorodifluoroethane; and fifluoroethane. The preferred propellants of the present invention are isobutane and propane. The preferred amount of liquified propellant is from about 20% to about 50%.

The present composition may also contain, as an optional ingredient, from about 0% to about 85% by weight of a volatile liquid carrier. Such liquids are in the liquid state at room temperature (about 22° C.) and evaporate completely from the skin within thirty minutes after applying the composition of the present invention onto the body. From these liquids a group of liquids have been selected which are organic in nature having a low degree of irritation and toxicity, that are generally considered safe for topical use, that provide for a controlled deposition on the skin of the polyester of the present invention polymers used in the present composition, that allow for the formation of a continuous polymeric film of polyester of the present invention polymer and active sunscreen agents are hereinafter referred to as volatile liquid carriers of the present composition. Preferred volatile liquid carriers include but are not limited to cyclic dimethylpolysiloxanes (volatile silicones), trichlorofluoromethane, isopropanol and $C_{10}$–$C_{16}$ isoparaffins. The most preferred volatile liquid carriers are $C_{12}$–$C_{14}$ isoparaffins and volatile silicones. The preferred amount of the volatile liquid carrier is from about 35% to about 60% by weight.

The present composition may additionally contain, as an optional ingredient, from about 0% to about 20% by weight of water-insoluble materials having a water solubility of less than about 1% at 25° C. From these materials a group of compounds have been selected which are organic in nature having a low degree of irritation and toxicity, that are generally considered safe for topical use, that provide a softening or soothing effect on surface skin tissue are hereinafter referred to as the water-insoluble emollients in the present composition. Preferred water-insoluble emollients include fatty acids such as oleic and stearic; fatty alcohols such as cetyl, and hexadecyl (ENJAY); esters such as diisopropyl adipate and isononyl iso-nonanoate; alkanes such as mineral oil; silicones; such as dimethyl polysiloxane and ethers such as polyoxypropylene butyl ethers and polyoxypropylene cetyl ethers. The most preferred water-insoluble emollients are: diisopropyl adipate, dimethylpolysiloxane 50 cst. and polyoxypropylene (14) butyl ether. The preferred amount of water-insoluble emollient is from about 2% to about 15% by weight, and most preferrably from about 4% to about 10%.

The water-insoluble emollient can be used to control the rate of evaporation of the composition. In addition to providing emolliency, they also aid in controlling the amount of product deposited on the skin and the tackiness of the composition. One skilled in the art will easily be able to adjust the cosmetic aesthetics and physical characteristics of the composition by combining various suitable water-insoluble emollients in the proper proportions with the ingredients of the composition mentioned hereintofore.

The water-proof compositions of the present invention may be made in a variety of ways to those skilled in the art. One method for preparing compositions in the form of water-proof oils is to dissolve the active sunscreen agent in the polyester of the present invention with agitation in a suitable vessel until a complete solution is formed. Optional ingredients such as volatile liquid carriers and water-insoluble emollients may then be added and mixed until a complete solution is formed. The composition may then be placed in a suitable container.

A similar preparation may be employed for preparing anhydrous water-proof compositions in the form of lotions and creams. In this procedure the active sunscreen agent, polyester of the present invention and any optional ingredient with the exception of particulate suspended matter, are combined together in a suitable vessel with mixing and heated to about 75° C. at which time a thickening agent such as zinc stearate or polyethylene polymer is added and mixed until dissolved. The mixture is allowed to cool, which results in the formation of viscous lotion or a thick cream product. During the cooling process fragrance and the particulate matter can be added to the composition before thickening occurs.

Another procedure for preparing anhydrous water-proof compositions, in the form of aerosol sprays, is to dissolve the active sunscreen agent in the polyester of the present invention and combine the desired optional ingredients with agitation until a complete solution is formed. The mixture is then placed in a conventional aerosol container, affixed with a standard aerosol valve and pressurized with liquified propellant.

In another procedure, where it is desirable to prepare a water-proof composition in the forms of aqueous lotions and creams by emulsion formation, the polyester of the present invention, active sunscreen agent, surface active agent and any water-insoluble optional ingredient, with the exception of suspended particulate matter, are combined in a suitable vessel and heated to about 75° C. This portion of the composition is referred to as the oil phase. To a separate vessel, water and any water-soluble ingredient is mixed until a complete solution is formed and is also heated to 75° C. This portion of the composition is referred to as the water phase. When both phases are at 75° C., the water phase is added to the oil phase with agitation. The composition is cooled to a temperature between 40–65° C. at which time the suspended particulate matter and fragrance may be added if it is desired. The composition is further cooled to room temperature and placed in a suitable container.

A particularly preferred cosmetic formulation is a sun-screening composition. The composition typically contains 2% to 98% of the polyester as a vehicle and a sunscreening agent. Any active sunscreen agent, capable of absorbing the harmful effects of ultraviolet radiation which is non-irritating, non-toxic and is compatible with the ingredients used in the composition and which when applied to the skin are homogeneously dispersed throughout can be used. Active sunscreen agents that meet these criteria are: PABA (para-aminobenzoic acid); Cinoxate (2ethoxyethyl p-methoxycinnamate); diethano-lamine p-methoxycinnamate; digalloyl trioleate; Dioxybenzone (2,2'-dihydroxy-4-methoxybenzophenone); ethyl 4 [bis(hydroxypropyl)] amino-benzoate; 2-ethyl-hexyl 2-cyano-3,3-diphenylacrylate; ethylhexyl p-methoxycinnamate; 2-ethylhexyl salicylate; glyceryl aminobenzoate; Homosalate (3,3,5-trimethylcyclohexyl salicylate); menthyl anthranilate (menthyl o-aminobenzoate); Oxybenzone (2-hydroxy-4methoxybenzo-phenone); Padimate A (amyl p-dimethylaminobenzoate); Padimate O (octyl p-dimethylaminobenzoate); and triethanol-amine salicylate.

The sunscreen compositions of the present invention may contain from about 1% to about 30% by weight of these active sunscreen agents or a mixture thereof. The preferred total amount of the active sunscreen agent is dependent upon the SPF value (sun protection factor) desired to be obtained. The preferred sunscreen agents in the present invention are Padimate 0 in amounts from 2% to about 10% by weight; Padimate A in amounts from 1% to about 8% by weight; 2-ethylhexyl salicylate in amounts from 3% to about 8% by weight; ethylhexyl p-methoxy-cinnamate in amounts from 2% to about 8% by weight; Dioxybenzone from 1% to about 5% by weight and Oxybenzone from 1% to about 7% by weight.

In a further preferred embodiment of the present invention, an effective amount of an polymer described above is added to an anionic surfactant-containing hair or skin care product, preferably. Thus, the polymer compositions of the present invention can be used in, inter alia, shampoos, conditioners, rinses, coloring products, bleaching products, setting lotions, blow-drying lotions, restructuring lotions, perms and straightening products.

Aside from hair care uses, skin and nail conditioning products are desired which function to improve properties such as retention of moisture, softening of the skin, attraction of air moisture, retardation of water loss, feel and reduction of skin irritations caused by contact with cosmetic ingredients. Examples of such products include detergents, lotions and soaps.

The present invention is illustrated by the following Examples, but should not be construed to be limited thereto. In the Examples, "part" and "%" are all part by weight or % by weight unless specified otherwise.

EXAMPLE 1

Synthesis of Poly[(Lactic Acid)-Co-(Ricinoleic Acid)]

Into a one-liter four neck flask equipped with stirrer, thermometer, nitrogen gas inlet tube and water separator, were charged 89 grams of lactic acid (88% purity) and 308 grams of ricinoleic acid. The resulting reaction mixture was heated at 155°–160° C. for four hours with stirring while nitrogen gas was being blown therethrough. After completion of the reaction, the reaction product was washed with water, vacuum-dried, and deodorized with steam at reduced pressure to yield esters having the following properties: Acid Value (AV) 46.8; Hydroxy Value (46.8) and ester value of 233.

EXAMPLE 2

Synthesis of Poly[(Lactic Acid)-Co-(Ricinoleic Acid)] by Transesterification

Into a one-liter four neck flask equipped with stirrer, thermometer, nitrogen gas inlet tube and water separator, were charged 103.6 grams of lactic acid (88%), 315 grams of methyl ricinoleate and 0.8 grams of potassium carbonate. The resulting reaction mixture was heated at 155°–160° C. for four hours with stirring while nitrogen gas was being blown therethrough. After completion of the reaction, the reaction product was washed with water, vacuum-dried, and deodorized with steam at reduced pressure to yield polyesters having the following properties: Acid Value (AV) 9.2; Hydroxy Value (HV) 70.7 and ester value of 281.

EXAMPLE 3

Synthesis of Poly[(Lactic Acid)-Co-(Ricinoleic Acid)]

Into a two-liter four neck flask equipped with stirrer, thermometer, nitrogen gas inlet tube and water separator, were charged 302 grams of lactic acid, 800 grams of ricinoleic acid and 6.6 grams of sodium hypophosphite. The resulting reaction mixture was heated at 155°–160° C. for three hours and then at 190°–200° C. for about 68 hours with stirring while nitrogen gas was being blown therethrough. After completion of the reaction, the reaction product was washed with water, vacuum-dried, and deodorized with steam at reduced pressure to yield polyesters having the following properties: Acid Value (AV) 27.57; Hydroxy Value (HV) 12.46; and a saponification value of 319.47.

EXAMPLE 4

Synthesis of Poly[(Glycolic Acid)-Co-(Ricinoleic Acid)]

Into a one-liter four neck flask equipped with stirrer, thermometer, nitrogen gas inlet tube and water separator, were charged 76 grams of glycolic acid (90% purity) and 308 grams of ricinoleic acid. The resulting reaction mixture is heated at 150°–155° C. for six hours with stirring while nitrogen gas was being blown therethrough. After completion of the reaction, the reaction product was washed with water, vacuum-dried, and deodorized with steam at reduced pressure.

EXAMPLE 5

Synthesis of Poly[(Glycolic Acid)-Co-(Ricinoleic Acid)]

Into a two-liter four neck flask equipped with stirrer, thermometer, nitrogen gas inlet tube and water separator, were charged 250 grams of glycolic acid, 750 grams of ricinoleic acid and 5.6 grams of sodium hypophosphite. The resulting reaction mixture was heated at 155°–160° C. for three hours and then at 190°–200° C. for about 60 hours with stirring while nitrogen gas was being blown therethrough. After completion of the reaction, the reaction product was washed with water, vacuum-dried, and deodorized with steam at reduced pressure.

EXAMPLE 6

Synthesis of Poly[(4-Hydroxybutanoic Acid)-Co-(Ricinoleic Acid)]

Into a one-liter four neck flask equipped with stirrer, thermometer, nitrogen gas inlet tube and water separator, were charged 95 grams of 4-hydroxybutyric acid acid (90% purity) and 308 grams of ricinoleic acid. The resulting reaction mixture is heated at 150°–155° C. for ten hours with stirring while nitrogen gas was being blown therethrough. After completion of the reaction, the reaction product was washed with water, vacuum-dried, and deodorized with steam at reduced pressure.

EXAMPLE 7

Synthesis of Poly[(5-Hydroxypentanoic Acid)-Co-(Ricinoleic Acid)]

Into a one-liter four neck flask equipped with stirrer, thermometer, nitrogen gas inlet tube and water separator, were charged 110 grams of 4-hydroxypentanoic acid (90% purity) and 308 grams of ricinoleic acid. The resulting reaction mixture is heated at 150°–155° C. for ten hours with stirring while nitrogen gas was being blown therethrough. After completion of the reaction, the reaction product was washed with water, vacuum-dried, and deodorized with steam at reduced pressure.

EXAMPLE 8

Synthesis of Poly[(Salicylic Acid)-Co-(Ricinoleic Acid)]

Into a one-liter four neck flask equipped with stirrer, thermometer, nitrogen gas inlet tube and water separator, were charged 120 grams of salicylic acid (95% purity) and 308 grams of ricinoleic acid. The resulting reaction mixture is heated at 155°–160° C. for eight hours with stirring while nitrogen gas was being blown therethrough. After completion of the reaction, the reaction product was washed with water, vacuum-dried, and deodorized with steam at reduced pressure.

EXAMPLE 9

Synthesis of Poly[(6-Hydroxyhexanoic Acid)-Co-(Ricinoleic Acid)]

Into a one-liter four neck flask equipped with stirrer, thermometer, nitrogen gas inlet tube and water separator, were charged 130 grams of 6-hydroxyhexanoic acid (95% purity) and 308 grams of ricinoleic acid. The resulting reaction mixture is heated at 155°–160° C. for eight hours with stirring while nitrogen gas was being blown therethrough. After completion of the reaction, the reaction product was washed with water, vacuum-dried, and deodorized with steam at reduced pressure.

EXAMPLE 10

In order to examine the presence of primary irritating properties of the polyesters of the present invention to the human body, a closed patch test is performed as follows: After removing the horny layer and sebum from a skin area located on the flexion side of the forearm or upper arm, a 1×1 inch piece of lint cloth having a sample spread thereon Is applied to that skin area, overlaid by oilpaper, fastened with adhesive tape applied in parallel crosses, and then covered with a bandage. This test is carried out on 20 healthy subjects and examination is made after 24 hours, 48 hours and 1 week. In addition, the development of odor after application is tested as follows: About 0.2 g of sample is applied to a 2×2 inch area of the forearm and examined, by smelling, for odor after 10, 20 and 30 minutes as well as after 1, 4 and 8 hours. This test is carried out on 20 healthy subjects. The results of these tests indicate no irritancy or no odor development.

EXAMPLE 11

WATERPROOF SUNSCREEN GEL SPF 27

| Components | Wt % |
| --- | --- |
| SD Alcohol 40 | 71.3 |
| Poly[(lactic acid)-co-(ricinoleic acid)] | 2.0 |
| Octyl Methoxycinnamate | 5.0 |
| Benzophenone-3 | 6.0 |
| Octyl Salicylate | 5.0 |
| PPG-15 Stearyl Ether | 10.0 |
| Hydroxypropyl cellulose | 0.7 |

EXAMPLE 12

WATERPROOF SUNSCREEN GEL

| Components | Wt % |
| --- | --- |
| SD Alcohol 40 | 68.3 |
| Poly[(glycolic acid)-co-(ricinoleic acid)] | 2.0 |
| Octyl Dimethyl PABA | 8.0 |
| Benzophenone-3 | 6.0 |
| Octyl Saliclate | 5.0 |
| PPG-15 Stearyl Ether | 10.0 |
| Hydroxypropyl cellulose | 0.7 |

EXAMPLE 13

WATERPROOF SUNSCREEN GEL SPF 30

| Components | Wt % |
| --- | --- |
| SD Alcohol 40 | 68.8 |
| Poly[(lactic acid)-co-(ricinoleic acid)] | 2.0 |
| Octyl Methoxycinnamate | 7.5 |
| Benzophenone-3 | 6.0 |
| Octyl Salicylate | 5.0 |
| PPG-15 Stearyl Ether | 10.0 |
| Hydroxypropyl cellulose | 0.7 |

EXAMPLE 14

WATERPROOF SUNSCREEN GEL SPF 17

| Components | Wt % |
| --- | --- |
| SD Alcohol 40 | 57.5 |
| Poly[(lactic acid)-co-(ricinoleic acid)] | 3.0 |
| Octyl Methoxycinnamate | 7.5 |
| Benzophenone-3 | 6.0 |
| Octyl Salicylate | 5.0 |
| Diisopropyl adipate | 20.0 |
| Hydroxypropyl cellulose | 1.0 |

EXAMPLE 15

WATERPROOF SUNSCREEN GEL SPF 15

| Components | Wt % |
| --- | --- |
| SD Alcohol 40 | 56.5 |
| Poly[(lactic acid)-co-(ricinoleic acid)] | 4.0 |
| Octyl Methoxycinnamate | 7.5 |
| Benzophenone-3 | 6.0 |
| Octyl Salicylate | 5.0 |
| Diisopropyl adipate | 20.0 |
| Hydroxypropyl cellulose | 1.0 |

EXAMPLE 16

WATERPROOF SUNSCREEN GEL

| Components | Wt % |
| --- | --- |
| SD Alcohol 40 | 54.8 |
| Poly[(glycolic acid)-co-(ricinoleic acid)] | 3.0 |
| Octyl Dimethyl PABA | 8.0 |
| Benzophenone-3 | 6.0 |
| Octyl Methoxycinnamate | 7.5 |
| Octyl Salicylate | 5.0 |
| Diisopropyl adipate | 5.0 |
| PPG-15 Stearyl Ether | 10.0 |
| Hydroxypropyl cellulose | 0.7 |

EXAMPLE 17

INSECT REPELLING WATERPROOF SUNSCREEN GEL

| Components | Wt % |
| --- | --- |
| SD Alcohol 40 | 53.5 |
| Poly[(lactic acid)-co-(ricinoleic acid)] | 2.0 |
| Benzophenone-3 | 6.0 |
| Octyl Methoxycinnamate | 7.5 |
| Octyl Salicylate | 5.0 |
| Diisopropyl adipate | 5.0 |
| DEET | 10.0 |
| PPG-15 Stearyl Ether | 10.0 |
| Hydroxypropyl cellulose | 1.0 |

EXAMPLE 18

A liquid hairdressing was prepared by adding 20 parts of the polyester of Example 1 and 0.5 part of a perfume to 79.5 parts of ethanol/water (50/50) solution and stirring the mixture at 40° C. until a homogeneous solution was formed. The hairdressing thus obtained had an excellent hairdressing effect and permitted any hairdo to be achieved softly. Moreover, the hair could be shampooed easily and no attack on celluloid products was noted.

EXAMPLE 19

A water-dispersible pasty hairdressing was prepared by mixing 60 parts of the polyester of Example 2 with 25 parts of polypropylene glycol having an average molecular weight of about 2,000 and 14 parts of polypropylene glycol having an average molecular weight of about 700. To this mixture, one part of a perfume and an adequate amount of an antioxidant were added with stirring.

EXAMPLE 20

An astringent lotion was prepared by dissolving 0.8 part of alum, 4.0 parts of glycerol, and 6.0 parts of the polyester of Example 1 in 77.8 parts of purified water. To this solution, a solution of 0.2 part of a perfume and 1.0 part of polyoxyethylene oleyl alcohol ether in 10.0 parts of ethanol was added and mixed well.

Although the present invention has been described with reference to specific details of certain embodiments thereof, it is not intended that such detail should be regarded as limitations upon the scope of the invention, except as and to the extent that they are included in the accompanying claims.

What is being claimed is:

1. A biodegradable polyester of the formula:

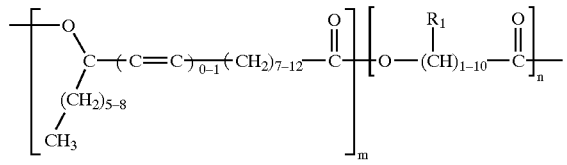

wherein R1 is selected from the group consisting of hydrogen and $C_{1-5}$ alkyl; m and n are independently integers from 1 to 100; m+n is an integer from 2 to 100 and wherein the ratio of m:n is from about 80:20 to about 20:80.

2. A biodegradable polyester according to claim 1 wherein the ratio m:n is from about 60:40 to about 40:60.

3. A biodegradable polyester according to claim 1 wherein the ratio m:n is 50:50.

4. A biodegradable polyester according to claim 1 selected from the group consisting of poly[(glycolic acid)-co-(ricinoleic acid)] and poly[(lactic acid)-co-(ricinoleic acid)].

* * * * *